us010275571B2

(12) United States Patent
Coffman et al.

(10) Patent No.: US 10,275,571 B2
(45) Date of Patent: Apr. 30, 2019

(54) DISTRIBUTED REMOTE ASSET AND MEDICATION MANAGEMENT DRUG DELIVERY SYSTEM

(75) Inventors: Damon J. Coffman, San Diego, CA (US); Timothy W. Vanderveen, Poway, CA (US); Bradford A. Lee, Encinitas, CA (US); David L. Schlotterbeck, Laguna Niguel, CA (US)

(73) Assignee: CareFusion 303, Inc., San Diego, CA (US)

(*) Notice: Subject to any disclaimer, the term of this patent is extended or adjusted under 35 U.S.C. 154(b) by 456 days.

(21) Appl. No.: 13/185,427

(22) Filed: Jul. 18, 2011

(65) Prior Publication Data

US 2011/0282691 A1 Nov. 17, 2011

Related U.S. Application Data

(60) Continuation of application No. 11/268,995, filed on Nov. 7, 2005, now Pat. No. 8,005,688, which is a
(Continued)

(51) Int. Cl.
*G16H 40/20* (2018.01)
*G06F 19/00* (2018.01)
(Continued)

(52) U.S. Cl.
CPC ........ *G06F 19/3462* (2013.01); *G06F 19/328* (2013.01); *G06F 19/3418* (2013.01);
(Continued)

(58) Field of Classification Search
CPC ............ G06F 19/3462; G06F 19/3418; G06F 19/322–19/328; G06Q 50/22–50/24; G16H 40/20
(Continued)

(56) References Cited

U.S. PATENT DOCUMENTS 2,141,006 A 12/1938 Marinsky
3,724,455 A 4/1973 Unger
(Continued)

FOREIGN PATENT DOCUMENTS

CA 2472098 A1 7/2003
CA 2554903 A1 4/2005
(Continued)

OTHER PUBLICATIONS

International Search Report and Written Opinion of the International Searching Authority dated Sep. 5, 2014 for PCT application PCT/US2014/037577.
(Continued)

*Primary Examiner* — Sheetal R Paulson
(74) *Attorney, Agent, or Firm* — Morgan, Lewis & Bockius LLP

(57) ABSTRACT

A system and method for communicating and validating patient information including medication delivery information in a care-giving facility is provided. A medical transaction carrier is used to communicate information regarding medication delivery and other patient information between a control system in communication with the care-giving facility's other information systems and a patient specific asset such as an infusion pump. All information carried by the medical transaction carrier is validated both at the patient specific asset and at the control system. This validation allows for positive control of all transactions even if a medical transaction carrier is lost. The medical transaction carrier may be a smartcard, a FDA such as a Palm™ Pilot, laptop computer, pager, mobile phone, or other device capable of storing and communicating information. The system may use either wired or wireless connections to communicate information between the components of the system.

10 Claims, 4 Drawing Sheets

Related U.S. Application Data division of application No. 09/860,865, filed on May 18, 2001.

(60) Provisional application No. 60/205,125, filed on May 18, 2000.

(51) Int. Cl.
*G06Q 50/22* (2018.01)
*G06Q 50/24* (2012.01)

(52) U.S. Cl.
CPC ............ *G06Q 50/22* (2013.01); *G06Q 50/24* (2013.01); *G16H 40/20* (2018.01)

(58) Field of Classification Search
USPC ........................................................ 705/2–3
See application file for complete search history.

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Singer et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen, III |
| 4,733,364 A | 3/1988 | Yamagata |
| 4,741,732 A | 5/1988 | Crankshaw et al. |
| 4,756,706 A | 7/1988 | Kerns et al. |
| 4,785,969 A | 11/1988 | McLaughlin |
| 4,788,449 A | 11/1988 | Katz |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkner et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Wojcicki et al. |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk et al. |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellegara et al. |
| 5,594,786 A | 1/1997 | Chaco et al. |
| 5,597,995 A | 1/1997 | Williams et al. |
| 5,601,445 A | 2/1997 | Schipper et al. |
| 5,622,429 A | 4/1997 | Heinze |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |

(56) References Cited

U.S. PATENT DOCUMENTS

| | | |
|---|---|---|
| 5,645,531 A | 7/1997 | Thompson et al. |
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers et al. |
| 5,721,913 A | 2/1998 | Ackroff et al. |
| 5,733,259 A | 3/1998 | Valcke et al. |
| 5,737,539 A | 4/1998 | Edelson et al. |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engleson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nellhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady et al. |
| 5,920,054 A | 7/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,985,371 A | 11/1999 | Fujioka et al. |
| 5,995,077 A | 11/1999 | Wilcox et al. |
| 6,000,828 A | 12/1999 | Leet |
| 6,003,006 A | 12/1999 | Colella et al. |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A * | 3/2000 | Holowko et al. ............. 235/380 |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,112,502 A | 9/2000 | Frederick et al. |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 * | 2/2003 | White et al. ..................... 705/3 |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 6/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts, Jr. et al. |
| 7,587,415 B2 | 9/2009 | Gaurav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |

(56) References Cited

U.S. PATENT DOCUMENTS

| | | |
|---|---|---|
| 7,771,385 B2 | 8/2010 | Eggers et al. |
| 7,771,386 B2 | 8/2010 | Eggers et al. |
| 7,776,031 B2 | 8/2010 | Hartlaub et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,962,544 B2 | 6/2011 | Torok et al. |
| 7,970,550 B2 | 6/2011 | Arakelyan et al. |
| 7,983,995 B2 | 7/2011 | Murphy et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,284,059 B2 | 10/2012 | Ross |
| 8,291,337 B2 | 10/2012 | Gannin et al. |
| 8,340,792 B2 | 12/2012 | Condurso et al. |
| 8,689,008 B2 | 4/2014 | Rangadass et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | DeLaHuerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1 | 6/2007 | Lynn |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0185615 A1 | 8/2007 | Bossi et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0099867 A1 | 4/2009 | Newman |
| 2009/0112333 A1 | 4/2009 | Sahai |
| 2009/0125335 A1 | 5/2009 | Manetta et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |

(56) References Cited

U.S. PATENT DOCUMENTS

| | | |
|---|---|---|
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0179006 A1 | 7/2012 | Jansen et al. |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0031976 A1 | 1/2014 | Reinhardt et al. |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1759398 A | 4/2006 |
| CN | 1803103 A | 7/2006 |
| CN | 101116077 A | 1/2008 |
| CN | 101146055 A | 3/2008 |
| CN | 201110955 Y | 9/2008 |
| CN | 101331491 A | 12/2008 |
| CN | 101689320 A | 3/2010 |
| CN | 101890193 A | 11/2010 |
| CN | 102068725 A | 5/2011 |
| CN | 102508877 A | 6/2012 |
| CN | 102521394 A | 6/2012 |
| CN | 102688532 A | 9/2012 |
| CN | 102799783 A | 11/2012 |
| DE | 4023785 | 1/1992 |
| EP | 0192786 A2 | 9/1986 |
| EP | 0384155 A2 | 8/1990 |
| EP | 0595474 | 5/1994 |
| EP | 0649316 A1 | 4/1995 |
| EP | 0652528 A2 | 5/1995 |
| EP | 0784283 A1 | 7/1997 |
| EP | 0921488 A1 | 6/1999 |
| EP | 1003121 A2 | 5/2000 |
| EP | 1018347 A2 | 7/2000 |
| EP | 1237113 A2 | 9/2002 |
| GB | 2 141 006 | 6/1987 |
| JP | S62114562 | 5/1987 |
| JP | H11505352 | 5/1999 |
| JP | 2002520718 A | 7/2002 |
| JP | 2003085283 A | 3/2003 |
| JP | 2004287616 A | 10/2004 |
| JP | 2006155070 A | 6/2006 |
| JP | 2008508616 A | 3/2008 |
| JP | H5168708 B2 | 3/2013 |
| KR | 1020070045611 A | 5/2007 |
| KR | 1020080013129 A | 2/2008 |
| KR | 100847397 B1 | 7/2008 |
| KR | 1020100125972 A | 12/2010 |
| KR | 20110070824 A | 6/2011 |
| KR | 1020120076615 A | 7/2012 |
| KR | 1020120076635 A | 7/2012 |
| NZ | 522631 A | 7/2004 |
| WO | WO-1993022735 A1 | 11/1993 |
| WO | WO-1994005344 A1 | 3/1994 |
| WO | WO-1994008647 A1 | 4/1994 |
| WO | WO-1994013250 A1 | 6/1994 |
| WO | WO 95/0023378 | 8/1995 |
| WO | WO-1996020745 A1 | 7/1996 |
| WO | WO-1996025214 A1 | 8/1996 |
| WO | WO 96/0036923 | 11/1996 |
| WO | WO-1997004712 A1 | 2/1997 |
| WO | WO-1998013783 A1 | 4/1998 |
| WO | WO-1998028676 A2 | 7/1998 |
| WO | WO-1999009505 A1 | 2/1999 |
| WO | WO 99/0010829 | 3/1999 |
| WO | WO-1999010830 A1 | 3/1999 |
| WO | WO-1999035588 A1 | 7/1999 |
| WO | WO-1999044167 A1 | 9/1999 |
| WO | WO-1999045490 A2 | 9/1999 |
| WO | WO-1999046718 A1 | 9/1999 |
| WO | WO-1999067732 A1 | 12/1999 |
| WO | WO 00/0003344 | 1/2000 |
| WO | WO-2000004521 | 1/2000 |
| WO | WO-2000018449 | 4/2000 |
| WO | WO-2000032088 | 6/2000 |
| WO | WO-2000032098 | 6/2000 |
| WO | WO-2001086506 | 11/2001 |
| WO | WO-2001088828 | 11/2001 |
| WO | WO-2002036044 | 5/2002 |
| WO | WO-2002069099 | 9/2002 |
| WO | WO-2003038566 | 5/2003 |
| WO | WO-2003053503 | 7/2003 |
| WO | WO-2003092769 | 11/2003 |
| WO | WO-2003094091 | 11/2003 |
| WO | 2004060443 A2 | 7/2004 |
| WO | WO-2004061745 A2 | 7/2004 |
| WO | WO-2010124016 A1 | 10/2010 |
| WO | WO-2010124328 A1 | 11/2010 |
| WO | WO-2012095829 A2 | 7/2012 |
| WO | WO-2014159280 A1 | 10/2014 |

OTHER PUBLICATIONS

Extended European Search Report for Application No. 14779655.1, dated Jul. 14, 2016, 8 pages.
Extended European Search Report for Application No. 14780320.9, dated Jul. 1, 2016, 7 pages.
U.S. Appl. No. 90/009,912, filed Aug. 12, 2013, Schlotterbeck et al.
U.S. Appl. No. 90/011,697, filed Aug. 12, 2013, Schlotterbeck et al.
"General-Purpose Infusion Pumps," Evaluation—Health Devices, Oct. 2002, pp. 353-387, vol. 31 (10), ECRI Institute.

(56) References Cited

OTHER PUBLICATIONS

"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Errors," electromedica, vol. 71, No. 1, 2003, pp. 2-10.
Eskew, James et al., Using Innovative Technologies To Set New Safety Standards For The Infusion Of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
International Search Reports and Written Opinions of the International Searching Authority dated Jun. 19, 2014 and dated Jun. 24, 2014 for PCT Application Nos. PCT/US2014/022840 and PCT/US2014/022832.
International Search Reports and Written Opinions of the International Searching Authority dated Jun. 18, 2014 and Jun. 19, 2014 for PCT applications PCT/US2014/022830, PCT/US2014/022835 and PCT/US2014/022837. Office Action issued in U.S. Appl. No. 13/802,683, dated Apr. 29, 2014, U.S. Appl. No. 09/860,865, dated Jul. 25, 2014, U.S. Appl. No. 13/802,446, dated Aug. 13, 2014 and U.S. Appl. No. 13/802,433 dated Aug. 25, 2014.
Canadian Office Action for Application No. 2512991, dated Mar. 2, 2017, 4 pages.
Extended European Search Report for Application No. 14801726.2, dated Jan. 5, 2017, 8 pages.
Calabrese, et al., "Medication administration errors in adult patients in the ICU," Intensive Care Med, 2001, pp. 1592-1598, vol. 27, Springer-Verlag.
Extended European Search Report for Application No. 14801713.0, dated Jan. 16, 2017, 8 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Extended European Search Report and Written Opinion for Application No. 14775918.7, dated Sep. 13, 2016, 10 pages.
Chinese Office Action for Application No. 201480015147.6, dated Mar. 10, 2017, 10 pages excluding translation.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, dated Mar. 2, 2018, 1 page.
Canadian Office Action for Application No. 2512991, dated Jan. 10, 2018, 4 pages.
Canadian Office Action for Application No. 2828898, dated Jan. 11, 2018, 8 pages.
Chinese Office Action for Application No. 201480015093.3, dated Jul. 16, 2018, 16 pages.
Non-Final Office Action dated Oct. 14, 2014, issued in U.S. Appl. No. 11/326,145, and Non-Final Office Action dated Oct. 24, 2014, issued in U.S. Appl. No. 13/559,537.
Chinese Office Action for Application No. 201480015025.7, dated Oct. 9, 2018, 27 pages.
Chinese Office Action for Application No. 201480015036.5, dated Sep. 29, 2018, 20 pages.
Chinese Office Action for Application No. 201480041362.3, dated Oct. 18, 2018, 13 pages.
Japanese Office Action for Application No. 2016-501081, dated Nov. 2, 2018, 6 pages.
Canadian Office Action for Application No. 2828898, dated Dec. 7, 2018, 5 pages.
Australian Office Action for Application No. 2014241022, dated Feb. 7, 2019, 4 pages.
Australian Office Action for Application No. 2014241019, dated Feb. 6, 2019, 3 pages.

\* cited by examiner

DISTRIBUTED REMOTE ASSET AND MEDICATION MANAGEMENT DRUG DELIVERY SYSTEM

This application is a continuation of U.S. application Ser. No. 11/268,995, filed Nov. 7, 2005 and now issued as U.S. Pat. No. 8,005,688, which is a division of U.S. application Ser. No. 09/860,865, filed May 18, 2001 and currently pending, which claims benefit of U.S. Provisional Application No. 60/205,125, filed May 18, 2000, all of which are incorporated herein by reference in their entirety.

BACKGROUND

The present invention relates generally to systems for managing patient care in a health care facility, and more particularly, to systems and methods for integrating and managing information with respect to medical care, medication delivery, asset identification, and verification of drug delivery.

Medication errors, that is, errors that occur in the ordering, dispensing and administration of medications, regardless whether those errors caused injury or not, have become a significant problem in the delivery of healthcare in the institutional setting. Additionally, adverse drug events ("ADE"), which are a subset of medication errors, defined as injuries involving a drug that require medical intervention, and representing some of the most serious medication errors, are responsible for a large number of patient injuries and death. A proportion of these errors are preventable, thus healthcare facilities continually search for ways to reduce the possible occurrence of medication errors. Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

Several companies are currently marketing or will be marketing hand-held personal digital assistants ("PDA") that are designed to provide drug administration scheduling, drug administration verification, and the electronic documentation drug administration. These devices are predominantly used to verify administration of oral, intramuscular ("IM"), subcutaneous, and topical drugs and have limited capability in verifying the administration of IV drugs. One disadvantage of these devices is they are currently incapable of monitoring or receiving data regarding the initial and ongoing infusion parameters of an intravenous ("IV") infusion device.

It is advantageous to have a care management system that combines all the various medication order and administration services of a healthcare facility into an integrated, automated system that checks and documents the delivery of therapeutic and other drugs to the patient. Such a system would prevent administering an inappropriate medication to a patient by checking the medication against a database of known allergic reactions and/or side-effects of the drug against the patient's medical history. The integrated system should also provide doctors, nurses, and other care-givers with updated patient information at the bedside, notify the facility's pharmacy when an additional drug is required, or when a scheduled treatment is running behind schedule, and automatically update the facility's accounting database each time a medication or other care is given.

In many hospitals and clinical laboratories, a bracelet device having the patient's identification such as his or her name printed thereon is permanently affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a nurse or technician may, instead of actually reading the patient's bracelet, miscopy the name or may rely on memory or a different data source.

Moreover, manually transferring other information such as parameters for configuring an infusion pump to dispense medication may result in errors that reduce the accuracy and/or effectiveness of drug administration and patient care. This may result in an increased duration of treatment with an attendant increase in cost.

Hospitals and other institutions continuously strive to provide quality patient care. Medical errors, such as where the wrong patient receives the wrong drug at the wrong time, in the wrong dosage, or even where the wrong surgery is performed, are a significant problem for all healthcare facilities. Many prescription drugs and injections are identified merely by slips of paper on which the patient's name and identification number have been hand-written by a nurse or technician who is to administer the treatment. For a variety of reasons, such as the transfer of patients to different beds and errors in marking the slips of paper, the possibility arises that a patient may be given an incorrect treatment. This results in increased expense for the patient and hospital that could be prevented using an automated system to verify that the patient is receiving the correct care. Various solutions to these problems have been proposed, such as systems that use bar codes to identify patients and medications, or systems allowing the beside entry of patient data. While these systems have advanced the art significantly, even more comprehensive systems could prove to be of greater value.

Delivery, verification, and control of medication in an institutional setting have traditionally been areas where errors can occur all too frequently. In a typical facility, a physician enters an order for a medication for a particular patient. This order may be handled either as a simple prescription slip, or it may be entered into an automated system, such as a physician order entry ("POE") system. The prescription slip or the electronic prescription from the POE system is routed to the pharmacy, where the order is filled, hopefully in a timely manner, so that the medication can be provided to the patient. Typically, pharmacies check the physician order against possible allergies of the patient and for possible drug interactions in the case where two or more drugs are prescribed, and also check for contra-indications. Depending on the facility, the medication may be identified and gathered within the pharmacy and placed into a transport carrier for transport to a nurse station. Once at the nurse station, the prescriptions are once again checked against the medications that have been identified for delivery to ensure that no errors have occurred.

Typically, medications are delivered to a nurse station in a drug cart or other carrier that allows a certain degree of security to prevent theft or loss of medication. In one example, the drug cart or carrier is divided into a series of drawers or containers, each container holding the prescribed medication for a single patient. To access the medication, the nurse must enter in the appropriate identification to unlock a drawer or door or container. In other situations, inventories of commonly used drugs may be placed in a secure cabinet located in an area close by a nurse station. This inventory may contain not only topical medications but oral, IM-, and IV-delivered medications as well. Nurse identification and a medication order number are typically required to gain access to the cabinet.

The nurse station receives a listing of drugs to be delivered to patients at intervals throughout the day. A nurse or other care-giver or other qualified person reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Common to all of these systems is the nurse or other care-giver who delivers the medication. The nurse or care-giver is central to the process of verifying that the right medication is given to the right patient in the correct dosage at the right time at the point of care. No other person in the facility is situated as well as the nurse or other care-giver delivering the medication to ensure or verify that the appropriate drug is being given to the appropriate patient.

Such a system works well to verify that patients are receiving the appropriate drug when drugs are delivered orally, but the system may not be capable of thoroughly verifying that the appropriate medication regimen is being delivered to a patient in the case where IV drugs are being delivered. For example, a nurse or other care-giver may carry an IV bag down to a particular patient area, hang the bag, program an infusion pump with appropriate treatment parameters and begin infusion of the medication. The applicable hospital control system, such as the pharmacy information system, may not know that the patient has received the medication, and if the information is lost somewhere, the possibility exists of medicating the patient twice. Thus, there may be a break in the link of verification that the medication is being properly delivered to the patient if an event occurs resulting in a deviation from the desired treatment parameters.

Hence what has been recognized as a need, and has heretofore been unavailable, is an integrated, modular system for tracking and controlling patient care and for integrating the patient care information with other institutional databases to achieve a reliable, efficient, cost-effective delivery of healthcare to patients. The invention fulfills this need and others.

SUMMARY OF THE INVENTION

Briefly, and in general terms, the present invention is directed to a new and improved information management system and method capable of monitoring, controlling and validating the administration of medical care delivery in a health care facility.

Generally, the system of the present invention includes a medical transaction carrier ("MTC") that contains information concerning past and present medical transactions. The medical transaction carrier is used to transfer information relating to past and present medical transactions between a control system that is interfaced with various other care-giving institutional information systems, such as a pharmacy information system, or hospital information system, or physician order entry system, or a patient specific asset located at a patient's bedside. The information transferred by the medical transaction carrier is used to validate that the right medication and the parameters of the medication administration record are properly delivered to the right patient. As is well known by those skilled in the art, the medication administration record ("MAR") is used by nurses to schedule medication administration. It is also used to document the actual administration of the medications. The medication order from the physician is recorded on the MAR, either by the pharmacy or the nurse staff members. As doses are administered, the nurse initials the corresponding time and records any additional required information (e.g. pulse rate, blood sugar). The MAR covets a specific period of time, typically 24 to 72 hours. The MAR is the legal record of drug administration, and it is kept as a permanent part of the patient's medical record. The system of the present invention includes methods for validating the information transferred by the medical transaction system to ensure that no information is lost.

The medical transaction carrier in accordance with one aspect of the present invention may be a personal data assistant ("PDA"), a laptop computer, a smart card, a BLUETOOTH transceiver, or other device capable of storing information and transporting the information from one location in a care-giving facility where medications are prepared for delivery to a patient's bedside. In another aspect, the medical transaction carrier may be primarily stationary and located at the patient's bedside. At the patient's bedside, the medical transaction carrier is interfaced to a patient specific asset ("PSA"), such as an infusion pump or vital signs monitor, and the information stored within the medical transaction carrier is communicated to the patient specific asset to provide the asset with specific treatment parameters to be used in delivering medication to the patient or in otherwise interacting with the patient.

In another aspect of the present invention, the patient specific asset may include a capability of monitoring the progress of the delivery of medication and storing information relating to the delivery of the medication in a memory. The stored information may then be communicated to the medical transaction carrier for transport back to the control system, where the information is transferred from the medical transaction carrier and validated and/or documented by the control system. Documentation may occur in the pharmacy system for example.

In a further aspect of the present invention, the patient specific asset is configured to validate that information related to past medical transactions has been communicated to the control system. The control system may also include a capability of validating information transferred from the patient specific asset to the control system to ensure that all transaction information stored in the patient specific asset has been transferred to the control system for storage in a data base. In more detailed aspects, the PSA retains such past medical transaction information until it is notified that the control system has validated the information.

In yet another aspect of the present invention, care-givers, patients and medications may be identified using bar coded labels, RF identification, BLUETOOTH tags, or other devices. Such other devices may include active devices such as embedded computers or passive devices, such as magnetic strips.

In still another aspect of the invention, information is communicated between the various components of the system using wireless technology. For example, the various components of the system may communicate using a wireless network utilizing communication protocols such as BLUETOOTH™ (IEEE 802.15) or other protocols such as those described in IEEE 802.11, 802.11a, and 802.11b. Communication within the wireless network may utilize radio frequency electromagnetic radiation, infrared radiation or other means for accomplishing wireless communication between network elements.

In yet another aspect of the invention, the MTC may take the form of an electronic data stream, or message, formatted to include a unique identifier identifying each individual message and medical transaction information as described with reference to a physical MTC. In this aspect, the PSA may be connected, either by a physical connection, or by wireless connection, to a communication network in communication with various care facility information systems, such as a pharmacy information system. A processor operably connected to the PSA, which may be included in the same case as the PSA, for example in the case of an infusion pump, is configured to validate that an electronic MTC is received and validated by the care facility's information system before clearing the MTC from a memory operably connected to the processor.

These and other advantages of the invention will become apparent from the following more detailed description when taken in conjunction with the accompanying drawings of illustrative embodiments.

DETAILED DESCRIPTION OF THE PREFERRED EMBODIMENTS

The present invention provides a system and method for monitoring, controlling and tracking the administration of care in a healthcare facility. Additionally, the present invention also provides for closing the loop on drug delivery and validation that the right treatment has been given to the right patient.

Figure 1:
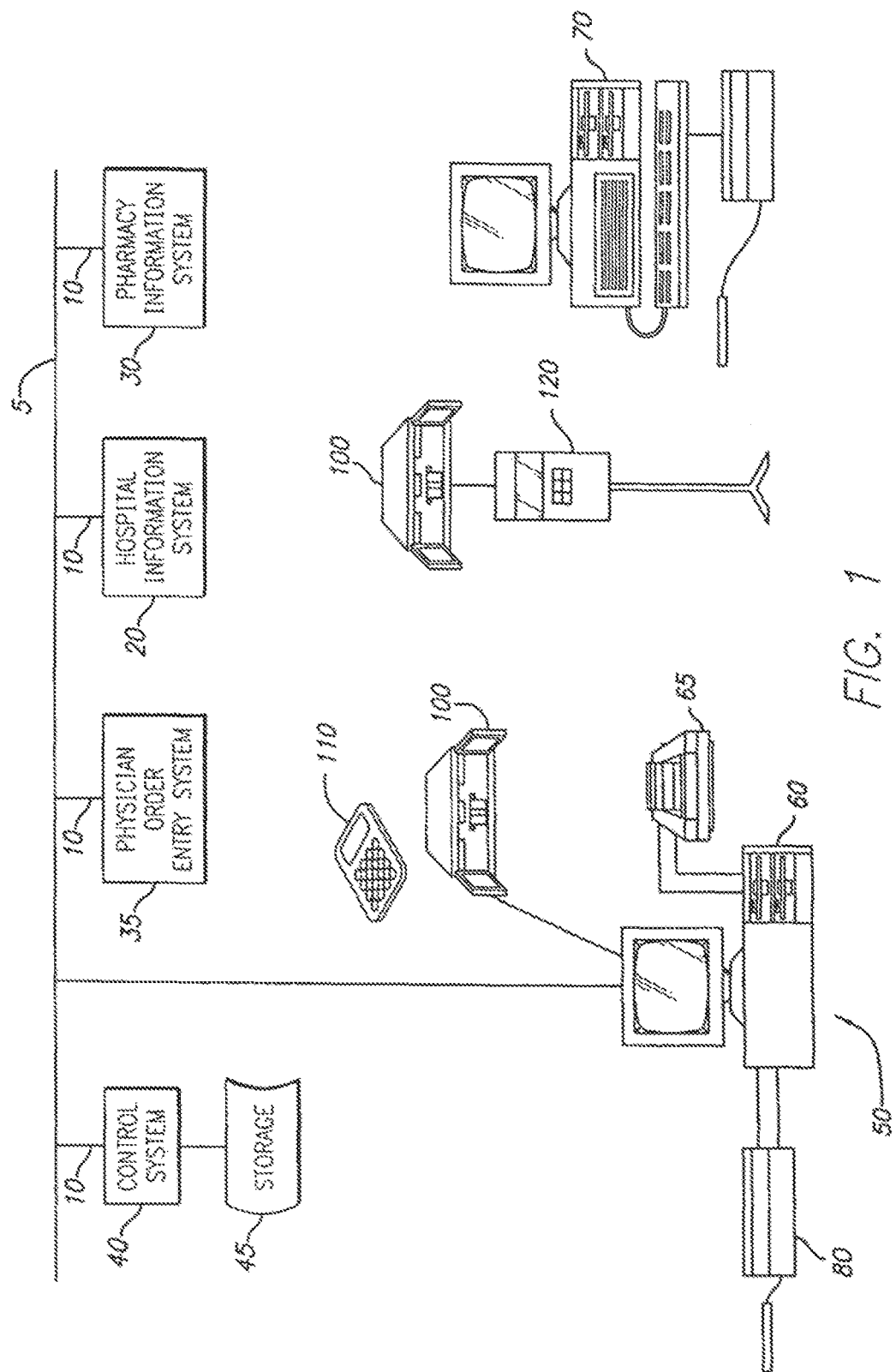
FIG. 1 is a graphical representation of a care management system incorporating principles of the present invention and illustrating details of the hardware elements and communications network, and the interconnections of the elements shown.

Referring now to drawings in which like reference numerals are used to refer to like or corresponding elements among the figures, there is generally shown in FIG. 1 an integrated hospital-wide information and care management system in accordance with aspects of the present invention. Various subsystems of an facility's information management system are connected together by way of a communication system 5. The communication system 5 may be, for example, a local area network (LAN), a wide area network (WAN), Inter- or intranet based, or some other telecommunications network designed to carry signals allowing communications between the various information systems in the facility. For example, as shown in FIG. 1, the communication system 5 connects, through various interfaces 10, a hospital information system 20, a pharmacy information system 30, a physician order entry system 35, and a control system 40.

The control system of the present invention may include various hardware components, such as a computer, for example, an IBM or IBM-compatible personal computer or server, having sufficient mass storage 45, such as local hard drives, CD-ROM, magnetic tape, or other media, and appropriate communication interface capabilities to interconnect with the communication system 5. Although many configurations are possible, in one embodiment, the control system 40 may include hardware such as a data communication router, modem, or other means for communicating with the hospital network. The control system 40 also includes software programs for carrying out various aspects of the present invention, as will be discussed more fully below, and basic operational software, such as an operating system such as Windows, Windows NT or Windows 2000 distributed by Microsoft, Inc., Linux, distributed by Red Hat or any other suitable operating system. The operational software will also include various auxiliary programs enabling communications with other hardware or networks, data input and output and report generation and printing, among other functions. While control system 40 is shown as a separate piece of equipment, it will be understood that control system 40 and mass storage 45 may also be incorporated into another element, such the pump 120 or other system.

The communication system 5 may comprise, for example, an Ethernet (IEEE 802.3), a token ring network, or other suitable network topology, utilizing either wire or optical telecommunication cabling. In an alternative embodiment, the communication system 5 may comprise a wireless system, utilizing transmitters and receivers positioned throughout the care-giving facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers. It will be immediately understood by those skilled in the art that such a system may be identical to the system set forth in FIG. 1, with the exception that no wires are required to connect the various aspects of the system.

In a typical hospital or other care-giving facility, patient rooms, wards, or areas are typically situated in groups located near a nurse station 50, where the nurses assigned to care for the patients in the particular area carry out the administrative functions of their duties. Typically, these functions include monitoring the patients' charts, preparation of medication orders, and monitoring and recording any other information deemed necessary to track by the facility. There is also usually a room located adjacent the nurse station that is dedicated to storage and/or preparation of medications to be delivered to patients. This room may contain inventories of commonly used oral, intramuscular or intravenous medications. Additionally, the room may also be used to formulate the contents of infusion bags in accordance with prescribed treatment regimens.

The nurse station 50 will typically include a terminal or computer system 60 connected either directly or through an interface (not shown) to the communication system 5, allowing users at the nurse station to enter and retrieve patient data or information from other systems, such as the hospital information system 20, the pharmacy information system 30, the physician order entry system 35, or other systems used in the facility. It should be understood that nor all users will be provided with access rights to each system. For example, physicians may be able to access the physician order entry system 35 from the nurse station system 50 to enter, edit or track medication orders, but a nurse may only be able to view such orders. Moreover, while the present invention is described with reference to the computer system 60 being located at a nurse station 50, the computer system 60 may also be a satellite system that is located anywhere in the care-giving facility where it is convenient or efficient to do so. Such a satellite computer system may be operably connected to the communication system 5 using either a wired or wireless network connection. A printer 65 may also be connected to the nurse station computer system 60 for printing reports, and a bar code reader 80 may be provided for reading bar codes on medication labels, reports or other items having bar coded labels provided for identification.

In the present invention, the nurse station computer system 60 includes a capability for providing data exchange between the computer system 60 and a medical transaction carrier device (MTC) 110. In one embodiment of the present invention, the MTC 110 may be interfaced to the nurse station computer system 60 through a cradle 100 or other docking device that provides a connection between the MTC 110 and the computer system 60. In this embodiment, use of the cradle 100 allows information to flow into and out of the MTC 110 to the computer system 60. This information may then be processed and stored on the computer system 60, or the information may be communicated by the computer system 60 to various other facility information systems over the communication system 5. In this manner, information from the pharmacy information system 30, for example, may be communicated through the communication system 5, the nurse station computer system 60, and the MTC cradle 100 into the MTC 110. Similarly, information contained within the MTC 110 may be communicated through the MTC cradle 100, the nurse station computer system 60, and the communication system 5 to any of systems 20, 30, 35, or 40.

The medical transaction carrier 110 generally refers to a device that contains medication and/or patient specific information that is portable such that it can be carried by a nurse or other care-giver to and from a patient's bedside. The MTC 110 may also have a storage capability and technology for interfacing with a computer system or network so that information may be communicated between the MTC 110 and other devices, such as computers, clinical devices and the like. The MTC 110 may, but not necessarily, include a processor.

It should be understood, however, that the general concept embodied in the MTC is to provide a way of communicating an order for medical care from a care facilities information system, such as a pharmacy information system or physician order entry system, to a patient specific asset, and communicating a message from the patient specific asset back to the information system that the order for medical care has been received by the patient specific asset. In another embodiment, the patient specific asset may also report that the order for medical care was actually carried out. The message from the patient specific asset is communicated to the relevant information system by means of the MTC and the information system "validates" the message from the patient specific asset with its copy of the order. As used herein, "validate" means "verify" or "corroborate." For example, the message from the patient specific asset may contain the unique order identifier. The information system compares that unique order number with order numbers in its memory and then indicates in its memory that a patient specific asset has received and or carried out the order. The order is then considered "validated" by the information system.

The patient specific asset includes a memory for storing the delivered order until it receives a signal or message from the information system that the message from the patient specific asset has been received by the information system, that the information system validated the order that was the subject of the message from the patient specific asset, and that the patient specific asset is therefore now authorized to clear the order from its memory. Thus, while various descriptions of a physically embodied MTC are provided as exemplary embodiments, it will be understood that an electronic message formatted to include appropriate information so that the validation by of the present invention may be carried out by operably connected information systems and patient specific assets processors is within the intended scope of the invention. More details of such a system are set forth in more detail below.

The MTC 110 typically will have stored within it data or information concerning various transactions representing the identity and treatment regimens for medications to be given to a patient, as well as other information, such as care-giver identity, equipment location, patient vital sign information, or any other information sought to be recorded. The MTC 110 may also store data or information concerning primary or secondary validation of previous and/or duplicate transactions of medical treatment information.

While specific examples of a MTC 110 are set forth herein, it will be understood that any device that carries out the basic concept of the invention, i.e., a device that carries patient specific and/or other medical or treatment information from a nurse station or other source of information to a patient, wherein the information may be downloaded or otherwise communicated to a patient specific asset, and which may in turn receive information from the patient specific asset, will accomplish the aims of the present invention. A particularly advantageous embodiment includes storing information in the MTC 110 until the MTC 110 re-establishes a communication connection with the control system 40, whereby the information stored in the MTC 110 may be communicated to the control system 40. In this manner, the present invention closes the loop ensuring that the right medication has been given in the right manner to the right patient.

For example, consistent with the present invention, the MTC 110 may be embodied in a hand-held "personal digital assistant" ("PDA") such as a Palm™ Pilot or a FDA running the Windows™ operating system, a notebook computer or other portable computer system. The MTC may also comprise a smartcard such as those that maintain account information and are issued by banking facilities, such as the American Express Bluecard. Other embodiments of the MTC may include a magnetic strip card, a PCMCIA card, RF-ID, or other non-volatile memory storage media. The use of such devices is advantageous in that devices having a suitably large memory to accommodate the type of information required by the present invention to track medication and validate treatment as well as retrieving other patient information, are readily available and relatively inexpensive, thus allowing a MTC to be assigned to each individual patient, or alternatively, to an individual clinical device. Additionally, such devices are small, compact and easily transportable.

In another embodiment, the MTC may comprise a pager device or a mobile telephone. Such devices would be particularly useful in a wireless environment, wherein the devices could be programmed to respond to signals from suitable transmitter/receivers located throughout the hospital.

Alternatively, the MTC 110 may be embodied in any device that includes an active embedded computer. Such an active embedded computer may be even smaller than a PDA or notebook computer. For the purposes of the present invention, such an active embedded computer includes any device incorporating a microprocessor and allows for input and/or output of information, whether via electrical, radio frequency or optical means, wireless or direct contact, and which contains its own power supply. One example of an active embedded computer in accordance with this invention may be attached to or embedded in the packing or container of a medication to be delivered to a patient. Such devices may typically be manufactured no larger than, for example, a postage stamp or business card and yet include, using micro circuitry, enough processing power, information storage, data or information input and output, and power to be suitable for use as a medical transaction carrier.

In yet another embodiment of the present invention, the medical transaction carrier may be a bar code label which contains information about the patient and the medication that is encoded into the bar code. Alternatively, the MTC may simply be an addressable information storage device, similar to memory "sticks" used as storage for digital cameras.

Medical transaction carriers in accordance with the present invention may be either stand alone, as where the MTC comprises a PDA, notebook computer or a smartcard, or alternatively, the MTC may be attached to another piece of equipment or device. For example, a medical transaction carrier using wireless technology could be incorporated into a medication carrying case or cart. Moreover, where the MTC is an electronic message, there need be no physical device used. Instead, a processor may be included in a patient specific asset that is configured to receive an electronic MTC, act on the information carried thereby, formulate a response message into an electronic MTC and transmit an electronic MTC to a facility's information system. Such a system would be understood to not be strictly portable, but rather stationary, in the sense that no physical device would be used to transport the medical transaction information contained in the MTC from one location to another. Instead, the electronic MTC may be transported either over a physical communications network, using, for example, wires or optical waveguides, or by way of a wireless network.

In another embodiment, such as where the patient specific asset is modular and includes an advanced programming module ("APM"), such as in the ALARIS Medical System, Inc. MEDLEY™ PATIENT CARE MANAGEMENT SYSTEM, the APM may include sufficient programming to perform the function of an MTC. In such case, the APM would be in contact with the relevant information system, such as the pharmacy information system, and would communicate to the information system that the patient specific asset received the order. The information system may then validate the order and communicate to the APM that the order has been validated. The APM may then delete the order from its memory.

It is not unusual at present to find computers 70 located at patient bedsides in a care-giving facility. Such computers 70 may serve a single patient, or may serve more than one patient, depending on the design and arrangement of the patient area. There may also be a variety of equipment or clinical devices attached to the bedside computer 70. Examples of such devices are a bar code reader 80, a printer (not shown), patient monitoring equipment (not shown) for monitoring patient vital signs or other patient specific assets ("PSA") assigned to the patient. Examples of such PSA's include an infusion device such as can form a part of the ALARIS Medical Systems, Inc.'s MEDLEY™ MODULAR PATIENT CARE SYSTEM. Attention is directed to U.S. Pat. No. 5,713,856 entitled "Modular Patient Care System" to Eggers et al. in which the APM is described as an advanced interface unit 100, and is incorporated herein by reference. In such system, an infusion device may be mounted to an Advanced Programming Module ("APM"). Other devices, such as a vital signs monitor or monitors, are envisioned as being mountable to the APM also. Other infusion or drug delivery devices and/or patient monitoring equipment such as cardiac or respiratory monitors may also comprise or form a part of the PSA.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside computer system 70, or, alternatively, they may be connected, either by wire or wireless system, to communication system 5 using wireless technology, such as RF, IR, or other wireless communication protocols.

One disadvantage of connecting the equipment or clinical devices directly into the communication system 5 or bedside computer 5 is that the PSA thus becomes immobile and relegated to a single location. This disadvantage is addressed by the present invention in that use of the MTC transport information to and from the clinical device or bedside equipment frees the device or equipment to be moved from one location to another without requiring changes to a communication network to identify the equipment or device, as is required where the equipment or device is identified as a node on the network.

In one embodiment of the present invention, the PSA 120 may include a MTC cradle 100. The MTC cradle 100 may be hardwired to the PSA 120 using the PSA's RS 232 or other communication port. Alternatively, the PSA 120 may include an integrated MTC cradle. Using such an integrated MTC cradle is advantageous in that it eliminates the need for another item of equipment that must be connected to the PSA. Of course, where PSAs having the required MTC cradle technology integrated therein are not available, an external MTC cradle 100 must be used. It will also be understood by those skilled in the art that, where an external MTC cradle 100 is necessary, the MTC cradle 100 may communicate with the PSA 120 using either wired or wireless technology, as described above.

As described previously, one particularly advantageous embodiment of the present invention includes a medical transaction carrier 110 that is capable of communicating information to and from the PSA 120 and the network or control system using wireless technology. For example, the MTC 110 may be understood to include, but is not limited to, communications utilizing optical or infrared transmission, magnetic transmission, or wireless technology where the wireless technology is understood to include methodology such as the BLUETOOTH™ technology (IEEE 802.15), standard methodologies such as wireless Internet, WAP or any other proprietary communication scheme using electromagnetic waves instead of wires to connect and communicate between devices. Such wireless communications may also be performed using other wireless networking alternatives, such as those described in the IEEE 802.11x standards. Wireless technologies are designed to create wireless networks allowing devices such as PDA's, cell phones and personal computers to exchange information at relatively high transmission speeds.

Using BLUE TOOTH™ technology, for example, data from a PDA, notebook computer, or other device such as a smartcard reader may be sent by an internal BLUE TOOTH™ radio chip embedded in the MTC 110 to a mobile telephone transmitter/receiver for transmission to a receiver connected to a server system. Using the IEEE 802.11x standards for example, data is transmitted directly to a receiver, which may be wired into a network using Ethernet or other network topology. The MTC is capable of wireless communication using either BLUE TOOTH™ or other technologies (such as those described in IEEE 802.11x), and may be used throughout a care giving facility without the disadvantage of requiring cumbersome hardwired devices.

One particular mode of operation of the present invention will now be described. A patient entering a hospital or other care giving facility is provided with a wristband, necklace, ankle band or other identifier that is affixed to the patient in a manner so that the patient can be identified even if the patient is unconscious or otherwise unresponsive. This wristband or other device may include a bar code representing the name of the patient and other information that the institute has determined is important. Additionally, any other information such as age, allergies, or other vital information may be encoded into the bar code. Alternatively, the patient information device may be an active embedded computer or passive device attached to a wrist band or other carrier that is attached to the patient. Such a device would be responsive to devices located throughout the care-giving facility, such as readers or wireless transmitter/receivers, to provide the identity of the patient along with other information when the device is queried.

After the patient is admitted and situated in a bed within the facility, the patient is typically evaluated by a physician and a course of treatment is prescribed. The physician prescribes a course of treatment by preparing an order which may request a series of laboratory tests or administration of a particular medication to the patient. In some case, the physician prepares the order by filling in a form or writing the order on a slip of paper to be entered into the hospital system for providing care. In other cases, the physician may enter the medication order directly into a physician order entry system 35 (FIG. 1) or may instruct a nurse or other care-giving professional to do so.

If the order is for administration of a particular medication regimen, the order will be transmitted to the facility's pharmacy information system 30. The pharmacy reviews the order, and prepares die medication according to the requirements of the physician. Typically, the pharmacy packages the medication in a container, and a copy of the order, or at a minimum the patients name, the drug name, and the appropriate treatment parameters are represented on a label that is affixed to the drug container. This information may be represented by a bar code, or it may be stored in a smart label, such as a label having an embedded computer or passive device.

Once the order has been prepared, the order is sent to the nurse station for matching with the appropriate patient. Alternatively, if the medication is for a commonly or routinely prescribed medication, the medication may be included in an inventory of medications that is stored in a secure cabinet adjacent the nurse station. In such a case, the nurse station will receive a list of orders from the pharmacy information system 30 that may be drawn from the inventory adjacent the nurse station. The nurse will enter here identifier at the cabinet to gain access, in accordance with standard practice. The nurse or other professional assigned the task of gathering medications will then match the orders received from the pharmacy information system 60 to the medications stored in the inventory and pull those medications that are to be delivered to specific patients. These procedures are carried out whether the medication to be delivered is an oral medication, or a medication that is to be delivered intramuscularly or through an infusion.

When the prescribed time for delivery of the medications arrives, the medications are carried to the patient's area and administered to the patient by the nurse or other care-giver in the case of drugs to be delivered via infusion, the care-giver hangs the infusion bag, attaches the bag to an infusion pump, and sets up the infusion pump to deliver the medication by programming the pump with values for various parameters that are used by the pump to control delivery of the medication to the patient. The infusion regimen is then started, and, because delivery of an infusion regimen generally extends over a prolonged period of time, the care-giver leaves the patient and continues on to care for other patients.

With the advent of modern infusion pumps that incorporate microprocessors and storage capability, it has become possible to maintain a record of not only the programmed infusion parameters, but also a log of the treatment as it is given to the patient. Until the present invention, however, there has been no way to ensure that the information gathered by the infusion pump was communicated to a system that could incorporate a record of the infusion into the patient's records stored in any of the facility's information systems.

Utilizing the present invention, a nurse or care-giver gathering or preparing medications to be delivered to patients programs a MTC 110 with the information appropriate to the particular medical treatment regimen that is to be delivered to a patient. Because medical transaction carriers are relatively inexpensive, there may be an individual MTC assigned to each patient or PSA 120. As will be discussed below, the MTC 110 provides for not only transporting information between care facility information systems and PSAs 120, but it also provides an instrument for validating the medical transaction to ensure that all information concerning delivery of a medication is retrieved and transferred to the care facility information systems. The system and method of the present invention accomplishes this in a manner that allows for loss of the MTC, or delay in return of the MTC or the use of different MTCs having different parts of a medical order without loss of information.

A communication session to transfer medical transaction information for a particular patient into a MTC 110 is initiated by inserting the MTC 110 into an appropriate slot or cradle for the MTC 100 which is in operable communication with the control system 40 via the nurse station computer system 60 and communication system 5. Alternatively, the MTC 110 may communicate with the control system 40 using a wireless system. As described above, this wireless system may comprise either infrared or RF frequency signals using appropriate communication protocols such as BLUE TOOTH™ or others (such as those described in IEEE 802.11x).

Once a connection has been established between the MTC 110 and the control system 40, the nurse or other care-giver preparing the medication logs into the control system 40 and the transaction may be tagged with the care-giver's unique identification. Alternatively, establishing communication between the MTC 110 and the control system 40 may automatically cause the system to query the care-giver for identification, which may be provided using an input device, such as a keyboard, bar code reader, or other device designed to read the care-giver's identification device.

The information to be transferred to the MTC 110 typically consists of orders for medication or other procedures that have been entered into an facility's information systems, such as the pharmacy information system 60. As each order, either for medication or other procedure, is entered into the facility's information systems, it may be given a unique transaction identifier. Thus, these identifiers may be associated with orders in a line-by-line manner such that each medication or procedure to be carried out on or delivered to a patient is uniquely identified by a unique transaction identifier. The medical transaction information, including the unique transaction identifiers in the facility information systems may be accessed by the control system 4 through communications system 5.

Once the medical transactions are assembled and available for access by the control system 40, specific infusion delivery protocols, medication limits, time-based medication constraints, and/or other patient's specific information comprising the medical transaction information may be transferred to the MTC 110. The amount of information transferred to the MTC 110 will be dependent only upon the software running on the control system 40, as well as the memory constraints of the MTC 110. Once the specific information has been downloaded from the control system 40 into the MTC 110, the MTC is ready to accompany the medication to the patient area for treatment of the patient.

In one embodiment, a single MTC may be assigned to a nurse to cover all the nurse's patients. Thus, the control system 40 may load all medical orders for a particular nurse for that day or for that nurse's rounds, on a single MTC assigned to that nurse.

In another embodiment, more than one MTC may be used to transmit an order or orders for a particular patient or patients. Where multiple MTCs are used, the various elements of the system of the present invention are programmed to determine whether all of the medical transaction information contained on the multiple MTC has been received and validated. Where one or more MTCs of a multiple MTC transaction have not been received or validated, the system of the present invention is configured to provide an alert to care givers in the care facility that corrective action is needed.

At the patient location, the information from the MTC 110 is transmitted to the PSA 120 using either wired or wireless technology. In one embodiment, the PSA 120 may be specifically configured to receive the MTC 110 to make the connection for transferral of data from the MTC 110 to the PSA. For example, where the MTC is a smart card, the PSA may include a slot or other device configured to receive the MTC 110 and to engage the MTC in such a manner as to allow communication between the MTC 110 and the PSA. Various methods for configuring such a communication connection are well-known in the art and will not be discussed herein, but may include, for example, connector pads or an induction coil capable of interfacing with the smart card to enable communication of information between the smart card and the PSA 120.

In an alternative embodiment, where the MTC 110 is a smart card having a magnetic strip, the PSA 120 may include a magnetic strip reader capable of reading the encoded information stored in the magnetic strip of the MTC 110. In yet another embodiment, the MTC may include a transmitter/receiver configured such that when the MTC 110 comes within a predetermined distance of the PSA 120, a communication link between the MTC 110 and the PSA 120 is automatically established. Using a unique identifier associated with the specific PSA 120 to be used to deliver the medication, the MTC 110 may query the PSA 120 to determine if the unique identifier stored in the memory of the MTC 110 matches that of the PSA 120. If the unique identifier stored in the MTC 110 does not match the identifier transmitted to it by the PSA 120, an error signal may be generated alerting the care-giver that the MTC 110 is communicating with the wrong PSA 120, and that the patient may receive the wrong medication.

If the MTC 110 queries the PSA 120 and receives a matching identifier, the MTC 110 begins communicating information into a memory of the PSA 120. This information may then be utilized by the PSA 120 to set the particular treatment parameters that are to be used to deliver medication to the patient.

The MTC 110 may also query the PSA 120 for historical records stored in the memory of the PSA. In this process, information such as a current key log, error log, vital signs log, infusion delivery log, medication delivery log, transaction identification, maintenance log and other logs and/or other patient data may be transferred from the PSA 120 to the MTC 110.

Additionally, the MTC 110 may remain in communication with the PSA 120 for the duration of the treatment, although the communication link between the MTC 110 and the PSA 120 may also be broken by removing the MTC 110 from the PSA 120 or cradle 100. At some time in the future, when the nurse or other care-giver is making rounds of the patients and determines that the treatment is over, communication between the MTC 110 and the PSA 120 may be reestablished. Before the MTC 110 is removed from the proximity of the PSA 120 at the end of the treatment, the nurse or other care-giver instructs the PSA 120 to transfer desired information, such as that described above, to the MTC 110. The MTC is then removed from the PSA 120 or from the cradle 100 attached to the PSA 120 and is carried by the nurse or care-giver back to the nurse station computer system 60 or other satellite computer system capable of reading the information stored in the MTC 110.

Once at the nurse station computer system 60, the MTC 110 in inserted into computer system 60 or MTC cradle 100, depending on the configuration of the equipment, to begin the process of communicating the patient information gathered from the PSA 120 into the storage of control system 40. Alternatively, particularly in the case where a wireless system is used, MTC 110 may be activated as it approaches within a predetermined distance of the nurse station computer system 60 or another other device, such as a computer system located at a location other than at the nurse station 50 (not shown) or a remotely located transmitter/receiver configured to establish communication with a MTC, to establish a communication connection with control system 40 over communication system 5.

Figure 2:
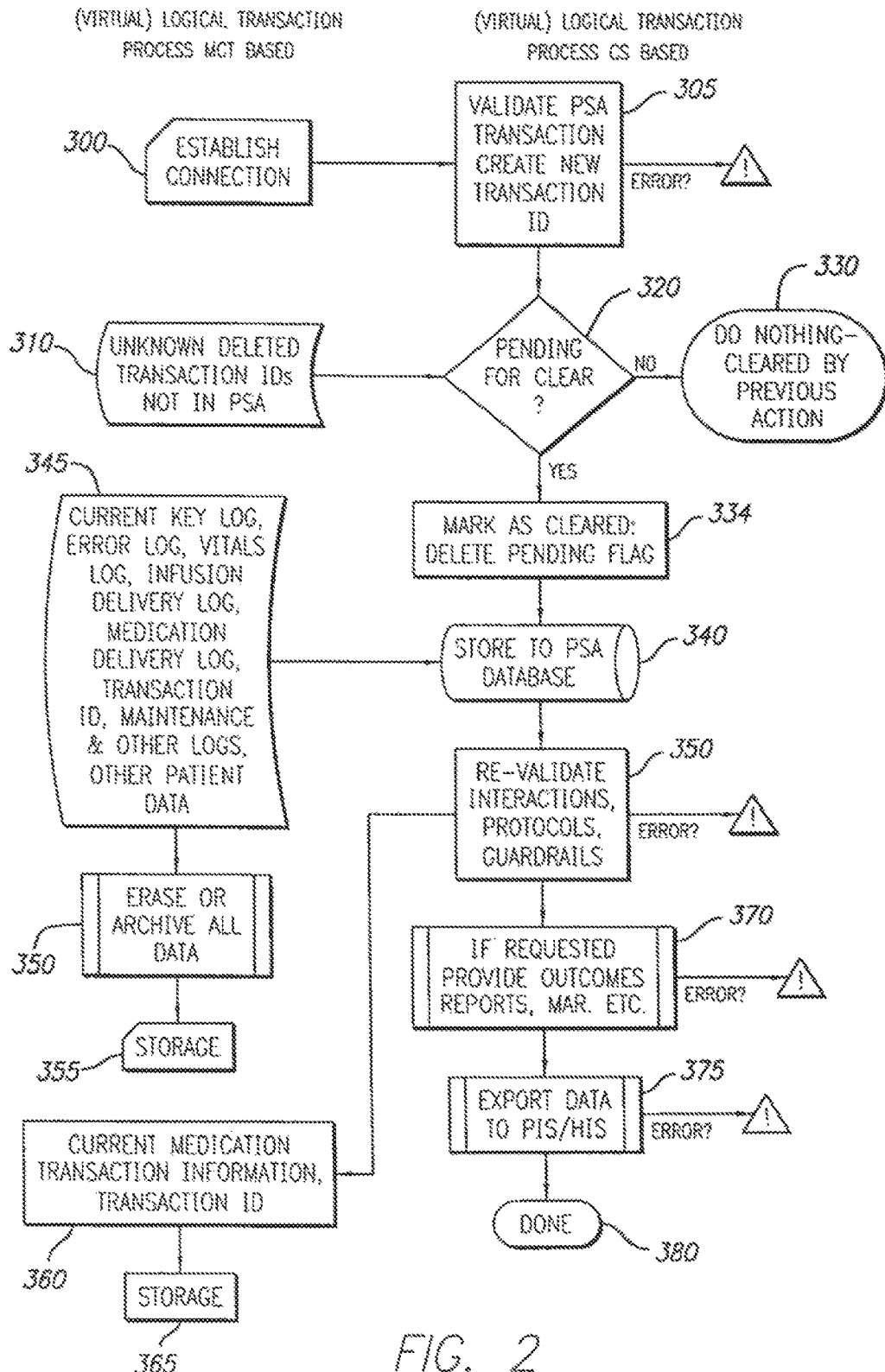
FIG. 2 is functional block diagram illustrating information flow between a medical transaction carrier and a control system of the present invention.

FIG. 2 is a block diagram of one method utilizing the system of the present invention illustrating the use of a medical transaction carrier 110 (FIG. 1) that is transported by a nurse or other care-giver to the location where the medication is to be delivered in communication with a patient specific asset that is to be used to deliver the medication and to retrieve medical transaction information concerning present and past medication delivery from the PSA. While the method is described with reference to programming the MTC 110, it will be understood that such programming also includes simply storing information in the MTC 110, and does not require that the MTC be capable of processing or running a program as those terms are often used in computer technology.

As described previously, the MTC 110 establishes a connection with the controlling server 40 in box 300. The controlling server 40 validates that this is a transaction with information from a PSA, and creates a new transaction ID for the particular transaction being undertaken in box 305. In the event that validation cannot occur, the control server 40 issues a signal to alert a nurse or care-giver that there is an error so that appropriate action to remedy the error may be taken.

Once the connection has been established in the box 300, the MTC 110 may be queried by the control system 40 to transmit unknown deleted transaction identifications (IDs) that were not found in the information stored in the PSA 120. The control server 40 analyzes the unknown deleted transaction IDs, and determines, in box 320, whether or not these transactions are pending or may be cleared from memory. If the transactions associated with the undeleted transaction IDs are not pending, control server 40 determines, in box 330, that no action needs to be taken and that these transactions were cleared during a previous communication session. In the case where the determination in box 320 indicates that the unknown deleted transaction IDs are pending for clearance, the control server 40 marks the transaction as cleared 334.

Once the unknown deleted transaction IDs have been marked as cleared 334, the control system 40 sends a signal to the MTC 110 indicating that the control system 40 is now ready to receive current information. This step may also be automated, for example, where the MTC 100 includes a processor capable of executing a series of program steps independent of the control system 40, such that the MTC 110 queries the control system 40 to determine if the control system 40 is ready to receive information. In the event that the query receives a positive response, the MTC 110 may then begin transferring current medical transaction information. Where the MTC 110 does not receive a positive response from the control system 40, indicating that the control system 40 is not yet ready to receive information, then the MTC 40 continues to wait and query the control system until it receives a positive response.

Once the transfer of information and/or data from the MTC 110 to the control system 40 has been initiated in box 345, information stored in the MTC 110 representing such information as, for example, but not limited to, a current key log, an error log, vital signs log, infusion delivery log, medication delivery log, transaction ID, maintenance and other logs, and any other patient data is communicated to the control system 40, where it may be stored in a database 45 associated with the control system 40 in box 340. In this way, the medical transaction information communicated by the MCT 110 to the control system 40 may be permanently associated with a particular PSA.

Once the information contained within the MTC 110 has been transferred to the control system 40 in step 345, the currently cleared and transferred medical transaction information stored in the MTC 100 may be erased, as indicated in box 350. Alternatively, the information may be archived to storage media, such as magnetic tape, hard drives, floppy disks, and the like, as indicated in box 355.

The control system 40 executes software programs in box 350 that analyze the information recently received from the MTC 110 and communicate new information for present medication delivery transactions to the MTC 110. Such software programs may include re-validating the past interactions recorded in the MTC 110 against data already stored in the PSA database. Where the validation fails, an error signal may be generated by the control system 40 causing a display or paper report to be printed notifying nurses or other care-giving personnel that an error exists.

Additionally, the software running on the control system 40 may analyze newly entered medical transaction information, such as the name or type of drug, dosage and delivery parameters, for example, against standard delivery protocols stored in the hospital or pharmacy information systems 20, 30 as well as determining whether there are any drug interactions or other safety information, such as may be stored in database that should be brought to the care-giver's attention and/or stored in the MTC 110. The software provides for generating error signals or alerts if errors or safety problems are detected during this step.

Once the current transaction data is analyzed, the control system 40 communicates the transaction information to the MTC 110. This information, as indicated in box 360, may include current medical transaction information and a unique transaction identification. This information is stored in the memory of the MTC 110 in box 365.

As indicated by box 370, the software running on the control system 40 may, if desired, generate various reports such as outcome reports, medical administration records or any other report requested by care-giving personnel or administrators. Any errors identified during the generation of these reports would result in an error signal that may either be displayed on a screen or printed in a printed report.

Additionally, as illustrated in box 375, the control system 40 may export all of the information transferred from the MTC 110 to the pharmacy information system 30 or hospital information system 20 for further processing or storage. Alternatively, the control system 40 may be programmed to export a selected portion of that data to those systems. Again, software running on the control system 40 may be executed to compare information stored on the various information systems 20, 30 and 35 with information gathered by the control system 40 and validate that the information is correct, with any failures in validation indicated by an error signal generated by the control system 40 to alert care-givers that a condition exists that may need attention and correction.

Once the previous steps have been undertaken to transfer information from a MTC to the control system for past transactions and transfer information concerning present medical transactions to the MTC have been completed, the process terminates at box 380. After terminating the process for a particular MTC 110, the process is repeated for each MTC 110 to be used to deliver medication in the care giving facility.

Figure 3:
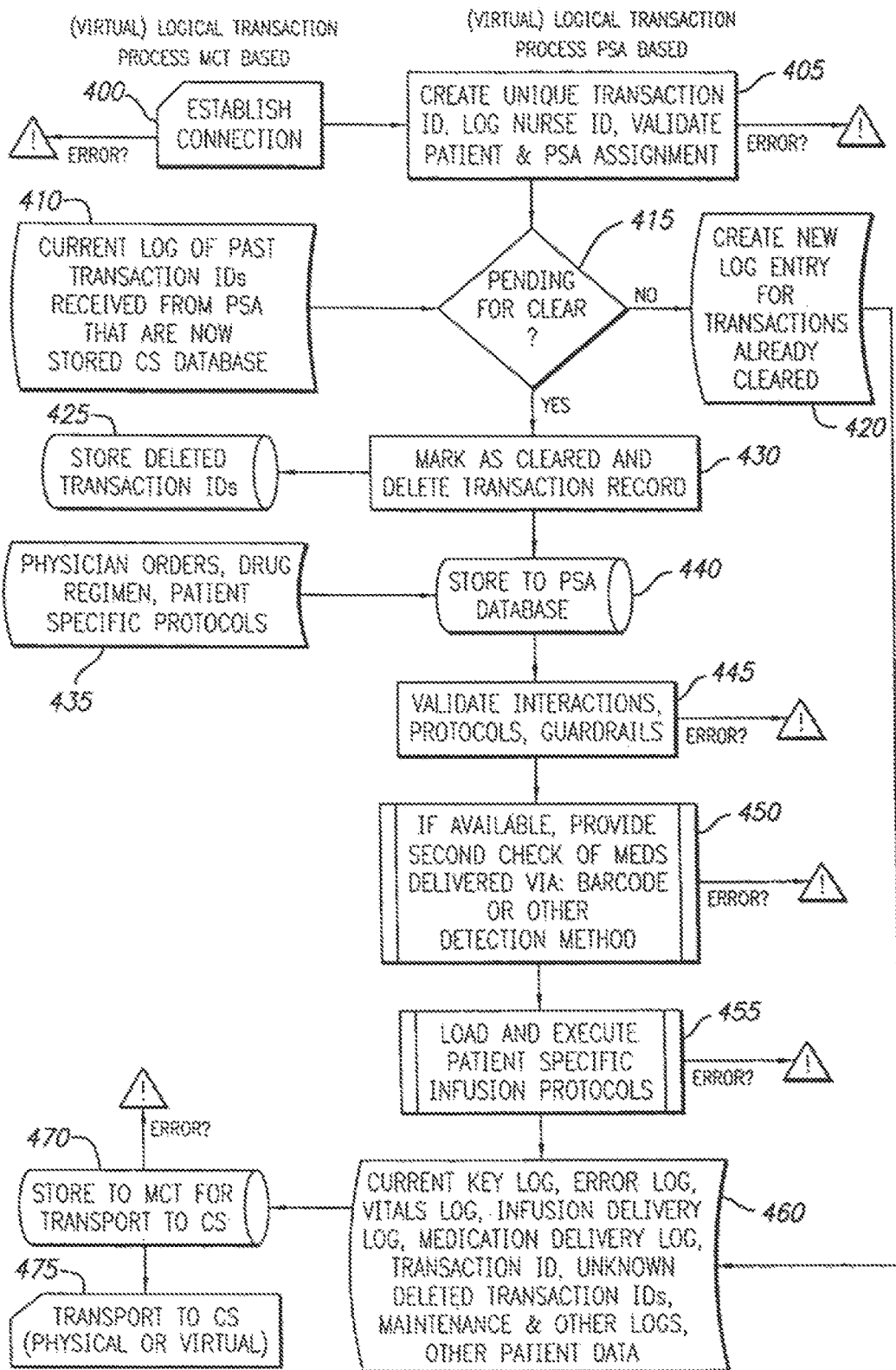
FIG. 3 is a functional block diagram illustrating information flow between a medical transaction carrier and a patient specific asset of the present invention.

Referring now to FIG. 3, a block diagram depicting one embodiment of a process illustrating various interactions between a MTC 110 and a PSA 120 located at a patient's bedside to communicate information between the MTC 110 and the PSA 120 is illustrated. The MTC 110 establishes a connection in box 400 with the PSA 120. If a connection cannot be established, an error signal is generated to alert the care-giver that corrective action must be taken before transfer of information between the MTC 110 and the PSA 120 may occur.

Once the connection has been satisfactorily established in box 400, the PSA 120 takes control of the process and creates a unique transaction ID, logs the care-giver's ID, and validates the patient and the PSA assignment in box 105. If any of the information is incorrect, the PSA 120 generates an error signal which may cause a message or code to be displayed by the PSA 120 or on a display associated with MTC cradle 100.

When the processes depicted in box 405 have been completed, the PSA 120 may signal the MTC 110 that it is ready to receive additional data from the MTC, and the MTC, in box 410, transmits a current log of past transactions ID's received from the PSA that are now stored in the control system database. Alternatively, the PSA 120 may simply address the memory of the MTC 110 and retrieve information from that memory without requiting any active participation by the MTC 110. The PSA 120 then determines, in box 415, whether or not any of the current log of past transaction ID's are flagged as pending for clearance.

If none of the current log of past transaction ID's are pending for clearance, the PSA 120 creates a new log of transactions already in box 420 and the process branches to box 460. If the current log of past transaction ID's are determined to be pending for clearance, then those transactions are marked as cleared and deleted from the pending transaction log in box 430, and are transmitted to the MTC 110 where they are stored in the memory of MTC 110 in box 425. The deleted transactions may be stored in the PSA 120 database, as indicated by box 440.

Once the deleted transaction identifications have been stored in the MTC memory, information comprising physician orders, drug regimens and patient's specific protocols for currently planned or scheduled medical treatments are transferred to the PSA 120 from the MTC 110 in box 435, and stored in the database of the PSA 120 in step 440. After the current physician orders, drug regimens, and patient specific protocols have been stored in the PSA 120 database, a software program may be run in the PSA to validate delivery protocols, drug interactions, and safety information, such as described earlier with reference to a database to ensure safe delivery of the medication to the patent in box 445. If any errors or safety issues are detected, an error signal is generated that may be displayed by the PSA 120, or on a display associated with the MTC cradle 100.

Where medication identification technology such as a bar code an embedded chip, or other identification method is available, a second check of the medication to be delivered may be accomplished as illustrated by box 450. If an error is detected in box 450, the care-giver is provided with an error signal indicating that corrective action is needed.

Once the validations carried out in boxes 445 and/or 450 are completed, a processor in the PSA 120 loads and executes the patient specific infusion protocols transferred to it by MTC 110 in box 455. Once again, if any errors are detected during this step, the care-giver is provided with an error signal indicating that corrective action is needed.

Information stored in the PSA 120 related to patient treatments may be communicated to the MTC 110 as depicted in box 460. For example, a current key log, an error log, a vital sign log, infusion delivery log, medication delivery log, transaction ID, unknown deleted transaction ID's, maintenance and other logs, and other patient data are may be communicated to the MTC 110 in box 460, where they are stored in the memory of the MTC 120 in box 470. Once the information is stored in the MTC 110, the MTC 110 may be removed from the PSA 120 or the MTC cradle 100 associated with the PSA 120 and transported to the control system 40, as illustrated by box 475. Such transportation may include physically carrying the MTC 110 to a specified location where the MTC 110 may be interfaced to and establish communication with the control system 40 and begin the download cycle described with reference to FIG. 2. Alternatively, if the MTC 110 is equipped with appropriate wireless technology, the transport to the control system 40 may become active either upon initiating the transmission by providing the MTC 110 with appropriate commands, or it may be automatically induced using a wireless system. For example, the MTC 110 may be supplied with a transmitter/receiver capable of automatically connecting to the communication system 5 to access the control system 40 using a wireless communication protocol such as BLUETOOTH™ or others (for example IEEE 802.11x).

It will be apparent from the above description that the validation steps carried out in the above process are independent of any one transaction. A transaction is not fully cleared from either the PSA or the control system until both the following occur:

(1) The system that originated a transaction receives validation of a transaction requested as executed; and (2) The system that receives the transaction request receives notification that the originating system has received and validated the transaction execution.

Because of this redundancy and validation, no transaction is cleared until it is certain that a transaction has been validated. Thus, in the event that a specific MTC 110 is lost, or the information stored therein is delayed in being communicated to the control system 40, each further action at a patient's bedside will retransmit the missing information until the control system database is properly updated. Utilizing this system, all medications received by the patient are logged into the control system database, as well as the actual time the medications were received. Moreover, the system ensures that the events log of all IV medications received and/or vital sign history are logged into die control systems database along with the identification of the nurse who gave the medications to the patient. Thus, full closed loop validation of data occurs. Utilizing this system, it will be apparent that the entire system functions in real-time in the critical direction, i.e. nurse to patient delivery of medication; and the system is near real-time in the non-critical direction, that is, from the patient's bedside back into control system, pharmacy information system and/or the hospital information system for closed loop validation of the medication delivery.

While the system of the present invention has be described with reference to the situation where patient medication and/or treatment is ordered using an facility's information system, and then delivered, the present invention is also applicable where treatment is care or medication is ordered orally by a physician or other care-giver at the patient's bedside, and is delivered to the patient before the order is entered into the facility's information system. In general, the oral order must then be entered into the facility's information systems within a predetermined period of time (typically 24 hours) to ensure that the medication administration record (MAR) is properly updated and accurately reflects the treatment given to the patient.

In the situation where care or medication is carried out before entry into the facility's information system, the patient specific asset, such as an infusion pump, stores in its memory the details of the care requested or the medication delivered, associating the care or medication details with a unique identifier generated by the patient specific asset. The next time the patient specific asset is in communication with a MTC 110, the patient specific asset transfers the care or medication details in the form of a medical transaction identified by the associated unique identifier to the MTC 110, which is then transported to the control system 40. When the medical transaction is transferred to the control system 40, the control system 40, using the unique identifier associated with the transaction by the patient specific asset, stores the medical transaction in the database 45. The control system 40 also generates a transaction indicating that the information has been received by the control system 40, and transfers that transaction to a MTC 110 that is to transported to the patient specific asset to communicate to the patient specific asset that the transaction has been received by the control system 40.

Once the transaction is stored in the database 45, the transaction may be matched by software running on the control system 40 of others of the facility's information systems to the entered oral order. If the transaction cannot be matched to an order, an alert may be provided indicating that: corrective action, in the form of entering the order into the facility's information systems or some other action, must be taken. In this manner, the loop is closed, ensuring that the oral order has been recorded and that the order has been carried out.

Alternatively, for example where, the patient specific asset is an infusion pump, the infusion pump may be programmed to sound an alarm after it has been infusing for a predetermined period of time, for example, an hour, and it has not received verification from the control system that a written order has been entered into the facility's information systems. Such an alarm may include stopping the infusion until an order is received, or may simply generate a visual and/or audible reminder that the order must be entered into the facility's information system or that a MTC 110 bearing an appropriate medical information transaction should be provided to the pump so that the pump may verify that the oral order has been entered.

In this embodiment, the oral order is entered into the information system, such as pharmacy information system 60, and is transferred to a MTC 110 which is then transported to the infusion pump. There, software running on the infusion pump compares the information in the transaction transferred to it by the MTC 110 to the information about the current infusion stored in the memory of the pump. If the information matches, the pump communicates to the MTC 100 a transaction indicating that it has received the order. This transaction communication is then transferred to the control system 40 to inform the control system 40 that the infusion pump has received the order.

Figure 4:
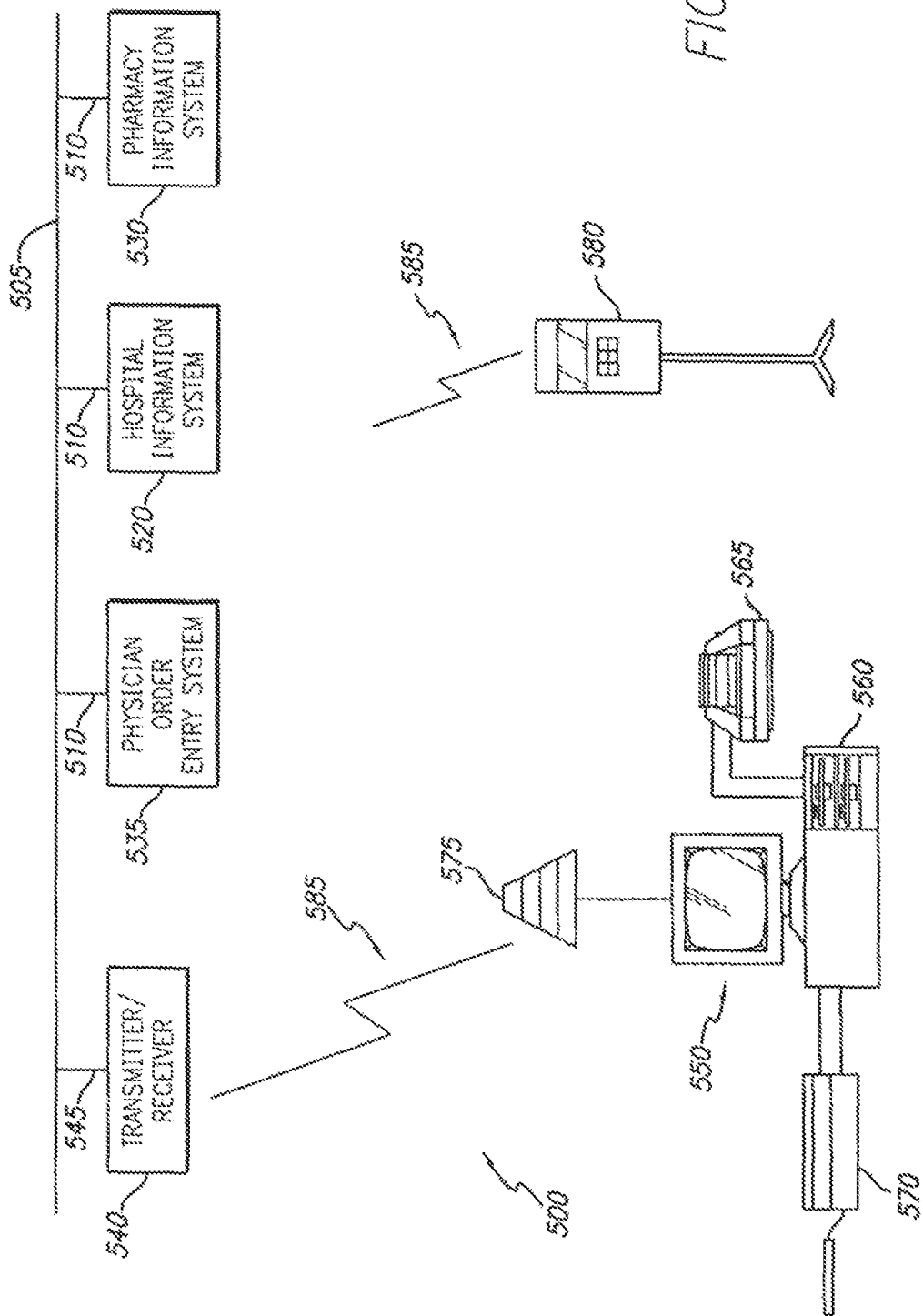
FIG. 4 is a graphical representation of another embodiment of a care management system of FIG. 1 wherein the control system is incorporated into a patient specific asset, which is in wireless communication with various care facility information systems.

Referring now to FIG. 4, an alternative embodiment of the present invention will be described that provides for transmission of MTC information from a care facility's information systems directly to a patient specific asset located at a patient's bedside. In the care management system 500 of this embodiment, a communication system 505 interconnects various care facility information systems, such as a hospital information system 520, a pharmacy information system 530 and a physician order entry system 535 via suitable interfaces 510. The communication system 505 and the interfaces 510 are similar to the communication system 5 and the interfaces 10 described with reference to FIG. 1, and those skilled in the art will understand, without further description here, that all of the embodiments discussed with reference thereto apply here.

The communication system 505 includes a connection to a wireless transmitter/receiver 540 through a suitable interface 545. The wireless transmitter/receiver 540 is configured to send messages using electromagnetic energy, which may include, for example, infrared energy or radio frequency radiation energy, between the communication system 505 and remote equipment and devices, such as a nurse station 550 and a patient specific asset 580, that are capable of receiving and transmitting messages using electromagnetic energy. For example, the nurse station 550 may be operably connected to a transmitter/receiver 575, and the patient specific asset may include a built in transmitter/receiver.

The nurse station 550 will typically include a computer system 560, a printer 565 and may further include an input/output device 570, such as a bar code reader, in addition to a keyboard of the type typically used with a computer. As described above, the nurse system computer system 560 may be operably connected to a wireless transmitter/receiver 575, or such a transmitter/receiver 575 may be incorporated into the computer system 560. Alternatively, the nurse station computer system 560 may be connected to the communication system 505 by means of a physical interconnection.

This embodiment of the present invention includes a patient specific asset 580 that includes a wireless transmitter/receiver that communicates with the various care facility information systems through the communication system 505 using electromagnetic energy 585. Alternatively, the patient specific asset 580 may be connected to a separate wireless transmitter/receiver or it may be connected with the communication system 505 using a physical interconnection.

The patient specific asset 580 also includes a memory for storing medical transaction information and a processor for analyzing medical transaction information transmitted to the patient specific asset 580 by the transmitter/receiver 540, instructing the device or devices comprising the patient specific asset 580 to carry out the medical care order contained within the medical transaction information, transmitting a message to the care facility's information systems that the medical care order contained in the medical transaction information has been received, storing the medical transaction information in a memory of the patient specific asset, and clearing the medical transaction information from the memory of the patient specific asset when the patient specific asset receives a message from an information system that it has received the patient specific asset's transmitted message. Such a processor may be operably connected to, and configured to communicate with and control, one or more clinical devices such as infusion pumps or patient vital sign monitoring equipment. One example of such a patient specific asset is the MEDLEY™ APM infusion controller module and related equipment manufactured by ALARIS MEDICAL SYSTEMS, INC.

It should be apparent from the above description that this embodiment of the present invention does not require a physical medical transaction carrier, as described with reference to FIG. 1. In this embodiment, the medical transaction carrier takes the form of a formatted electronic message that contains all of the information previously described with reference to physical medical transaction carrier. Each electronic medical transaction carrier is identified with a unique identifier that allows the information systems of the care facility and the processor associated with the patient specific asset 580 to communicate medical transaction information form the care facility's information systems to the patient specific asset, and to validate that a medical care order has been delivered to a patient. This embodiment provides for the closed system described in reference to a physical MTC, ensuring that each medical care order is delivered to the right patient at the right time, and that a record of that delivery is properly communicated to and received by the care facility's information systems. No medical transaction information is cleared from the memory of the patient specific asset 580, or marked as cleared in the facility's information systems, until the record of delivery of that care is validated in accordance with the present invention.

Additionally, where a system such as ALARIS MEDICAL SYSTEMS, INC.'s MEDLEY™ Patient Care Management System is used, a physician may enter an order using manual entry means, such as a key pad, associated with the APM. Because the APM is in communication with the various facility information systems, entry of the physician's identification may be considered equivalent to an electronic signature, and take the place of a written order.

The system and method of the present invention may also be enhanced by including technology that allows for real-time validation of the current patient utilizing a method to read or detect a patient identifier such as a wristband. For example, each patient may be identified by a wristband that includes certain specified information such as name, age, allergy history and the like that are encoded into a bar code. In one embodiment of the present invention, a bar code reader could be used to read the patient's bar codes at the same time that the MTC is transmitting its information to the PSA, thus ensuring that the right patient is receiving the right medication. Alternatively, the patient wristband could be replaced by a device that includes a transmitter/receiver or a passive device that could be activated using a suitable sensor to receive die above-described information from the patient's identification device.

Additionally, the system of the present invention may be enhanced by including technology that allows for real-time validation of each medication delivered to a patient. Such a system could include technology for reading a bar code applied to the medication, or could employ optical recognition, some form of active detection using a transmitter/receiver or smart chip or computer either embedded in the label of the medication or located on the medication container or other methods of positively identifying the medication. In this manner, the system further validates that each medication delivered to patient is identical to the medication that is indicated in the information contained within the MTC.

It should be apparent to those skilled in the art that the MTC may store and transport a wide variety of information useful to the care-givers and care-giving facilities for providing healthcare to patients. For example, the MTC may include a patient's unique ID, a nurse's unique ID, specific medication prescribed, and identification of the specific PSA assigned to a specific patient, the time of medication delivery, a current unique transaction ID identifying the current transaction of information between the MTC and the PSA, or the originator of the information such as the hospital information system or the pharmacy information system. Additionally, the MTC may also include past valid transactions for a particular PSA that are not yet validated by the PSA, and may also include past validated transactions for the PSA that have already been validated by the PSA. Moreover, the MTC, if it includes enough memory, may also be programmed to accept extra pharmacy preparation information as well as extra hospital maintenance or update information. Additionally, other information may be transmitted to and from the MTC as needed by the hospital administration, such as vital signs history and trend information.

The system concept will be understood to be the unique combination of all the previous elements into a seamless automatic methodology that requires no extra labor from the care-giver other than carrying the MTC's back and forth to the bedside as part of the care-giver's normal rounds. The system concept is enabled by the use of specific PC-based software with open database connectivity, MTC reader hardware at the point of medication preparation, and MTC reader hardware associated with patient specific assets. The system concept is effected through the use of remote transaction methodology similar to that employed in orbital communication satellite technology. Utilizing this methodology, data receipt and validation of data receipt and validated updated system status is acquired. This system concept is further effected by extending and combining the data validation concept with that used in packet-based data transfer, whereby specific data packets may be lost or duplicated, but the validation is still auditably correct. For example, if a particular MTC is not returned to the nurse station in a timely manner, information is not lost to the system. The two-way validation and check on all transactions ensures that eventually the information will make it back to the control system database when the MTC is eventually returned. In the event that a MTC is permanently lost, a time based alert could notify a care-giver to take appropriate action. Because of the redundancy of the system, it should be apparent that even if a specific MTC is lost or misplaced, the information contained in the PSA will eventually be returned to the control system for validation. The system of the present invention offers the additional advantage in that patient specific assets may be programmed such that the PSA will not perform a medication delivery regimen unless all of the safeguards and validations are carried out without error. In this manner, the possibility of error in delivering the wrong medication to a patient may be minimized at the bedside. Of course, in particular situations, such as where PSAs are utilized in operating room or emergency room environments, an override may be built into the PSA to allow emergency usage of the PSA when necessary.

While the PSA was described in terms of an infusion pump, the PSA, as described above, may also be a vital signs monitor or other clinical device interacting with a patient. For example, the patient specific asset may also be a patient feeding device.

Further, while automatic programming of a clinical device using a physical or electronic MTC is described, manual systems are also intended to be included within the scope of the system and method of the present invention. For example, some patient specific assets may exist within a facility that are capable of communicating with the control system 40 (FIG. 1) or a MTC, but which may not be capable of being programmed by signals received from a MTC or directly from control system 40. For those clinical devices that do not accept automatic programming, a nurse may read the medical transaction information from the MTC or from the device itself, program the device, then press a "START" or "ACCEPT" or other similar key on the device to indicate completion of programming. The clinical device may then communicate to the MTC information about the medical transaction it is performing for validation. The MTC may later communicate this information to the control system 40 for validation. Alternatively, the clinical device may communicate directly to the control system 40 information about the medical transaction it is performing for validation. This approach may also apply where a nurse takes a vital sign measurement, such as a patient's temperature. That temperature reading is input into the MTC either immediately or eventually, either directly from the thermometer in the form of a digital data stream, or manually by the nurse, and that medical transaction information will eventually be communicated to the control system 40. Similarly, this approach may be used were oral medications, such as aspirin, are dispensed.

Validation data from patient specific assets may reach the control system 40 via multiple MTCs. For example, different line items of a patient's order may be communicated to the patient's bedside patient specific assets via different MTCs. The control system 40 may validate the line items indicated as communicated to the PSA through different MTCs but will not clear the entire medical transaction information until it receives information concerning all of the line items. Thus, the control system will not send a message to the patient specific asset to clear the multiple line items from its memory until the control system 40 is satisfied that it has received information that all of the line items of the medical transaction have been carried out.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a hospital environment, it will be understood that the system and method may be useful in other environments as well, such as outpatient clinics and other environments where care is delivered to a patient.

While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. A system for remote managing drug delivery to a patient, comprising:
a care facility information system comprising a first memory storing a medical order for the patient;
a medical transaction carrier (MTC) device comprising a machine-readable code associated with a container of a medication, and information related to a delivery of the medication according to the medical order;
a patient specific asset (PSA) comprising an infusion pump configured to communicate with the MTC device to receive the code and information from the MTC and, based on receiving the information:
store medical order data for the medical order in a second memory,
automatically load and execute infusion protocols to deliver the medication to the patient;
determine that an operation performed by the PSA was carried out according to the infusion protocols and the medical order, and
automatically transmit, based on determining that the operation was carried out according to the medical order, an electronic message to the care facility information system over a network, the electronic message indicating that the operation was carried out according to the medical order.

2. The system of claim 1, wherein:
the stored medical order data comprises the code, and the code comprises a unique order identifier;
the electronic message comprises the unique order identifier; and
the care facility information system is configured to validate that the operation was carried out according to the medical order if the unique order identifier received corresponds to an order number of the medical order stored in the first memory.

3. The system of claim 2, wherein the care facility information system is configured to, based on validating the operation was carried out according to the medical order, provide a validation message to the PSA associated with the medical order, and
wherein the PSA is configured to, based on receiving the validation message, clear the medical order data from the second memory.

4. The system of claim 1, wherein:
the code is received by the MTC by a scanning of a label coupled to an intravenous (IV) container.

5. The system of claim 4, wherein:
the information comprises medication limits and time-based medication constraints for the infusion pump; and
the infusion pump is configured to set particular treatment parameters of the infusion pump according to the information.

6. A system for remote managing drug delivery to a patient, comprising:
a care facility information system comprising a first memory storing a medical order for the patient;
a medical transaction carrier (MTC) device comprising a machine-readable code associated with a container of a medication, and information related to the medical order;
a patient specific asset (PSA) comprising an infusion pump and a second memory, the PSA configured to communicate with the MTC device to receive the code and information from the MTC and, based on receiving the information,
automatically deliver the medication to the patient per the information,
store a record of a delivery of the medication in the second memory, and
automatically transmit, to the care facility information system over a network based on the medication being delivered to the patient, an electronic message indicating that the medication was delivered to the patient.

7. The system of claim 6, wherein:
the information in the second memory comprises a unique order identifier;
the electronic message comprises the unique order identifier; and
the care facility information system is configured to validate that the medication was delivered to the patient per the information if the unique order identifier corresponds to an order number of the medical order stored in the second memory.

8. The system of claim 6, wherein:
the care facility information system is further configured to send a message to the PSA in response to the care facility information system validating that the medication was delivered to the patient per the information; and
the PSA is further configured to clear the record of the delivery of the medication from the second memory upon receipt of the message.

9. The system of claim 6, wherein:
the code is received by the MTC by a scanning of a label coupled to an intravenous (IV) container.

10. The system of claim 9, wherein:
the information comprises medication limits and time-based medication constraints for the infusion pump; and
the infusion pump is configured to set particular treatment parameters of the infusion pump according to the information related to the medical order.

* * * * *

UNITED STATES PATENT AND TRADEMARK OFFICE
CERTIFICATE OF CORRECTION

| | | |
|---|---|---|
| PATENT NO. | : 10,275,571 B2 | Page 1 of 1 |
| APPLICATION NO. | : 13/185427 | |
| DATED | : April 30, 2019 | |
| INVENTOR(S) | : Coffman et al. | |

It is certified that error appears in the above-identified patent and that said Letters Patent is hereby corrected as shown below:

On the Title Page

IN THE ABSTRACT:
Item (57), In Line 13:
Replace "a FDA such as a Palm™", with --a PDA such as a Palm™--.

In the Specification

In Column 8, Line 45:
Replace "a FDA running the Windows™", with --a PDA running the Windows™--.

Signed and Sealed this
Sixteenth Day of July, 2019

Andrei Iancu
*Director of the United States Patent and Trademark Office*